United States Patent [19]

Hofmann

[11] Patent Number: 4,578,367

[45] Date of Patent: Mar. 25, 1986

[54] METHODS FOR REPROCESSING COBALT CATALYSTS USED IN HYDROCARBOXYLATION

[75] Inventor: Peter Hofmann, Marl, Fed. Rep. of Germany

[73] Assignee: Chemische Werke Hüls Aktiengesellschaft, Marl, Fed. Rep. of Germany

[21] Appl. No.: 702,658

[22] Filed: Feb. 19, 1985

Related U.S. Application Data

[60] Division of Ser. No. 516,435, Jul. 25, 1983, Pat. No. 4,521,526, which is a continuation-in-part of Ser. No. 203,393, Nov. 3, 1980, abandoned.

[30] Foreign Application Priority Data

Dec. 12, 1979 [DE]  Fed. Rep. of Germany ....... 2949878
Dec. 12, 1979 [DE]  Fed. Rep. of Germany ....... 2949939

[51] Int. Cl.$^4$ ..................... B01J 31/40; C07C 67/38; C11C 3/02; C09F 5/08
[52] U.S. Cl. ..................... 502/24; 260/410; 260/410.6; 260/410.9 R; 502/28; 560/233
[58] Field of Search .................. 502/24, 28, 53; 260/410.9 R, 410.9 C; 560/233; 423/139; 75/0.5 A, 119

[56] References Cited

U.S. PATENT DOCUMENTS

| | | | |
|---|---|---|---|
| 3,298,779 | 1/1967 | Goto et al. | 423/129 |
| 3,507,891 | 4/1970 | Hearne et al. | 260/410.9 R |
| 3,856,832 | 12/1974 | Keblys | 260/410.9 R |
| 3,883,587 | 5/1975 | Isa et al. | 560/233 |
| 3,906,016 | 9/1975 | Isa et al. | 260/410.9 C |
| 3,935,228 | 1/1976 | Keblys | 260/410.9 R |
| 4,041,057 | 8/1977 | Fanning | 260/410.9 R |
| 4,225,458 | 9/1980 | Huang | 502/24 |
| 4,481,147 | 11/1984 | Hofmann | 260/410.9 R |

*Primary Examiner*—P. E. Konopka
*Attorney, Agent, or Firm*—Wells & Wells

[57] ABSTRACT

The catalytic cobalt compound used in the reaction of olefins with carbon monoxide and water or alkanols which employs an oxidizing treatment is reprocessed according to the present invention. This reprocessing includes in a first embodiment treating the cobaltic residue obtained as the distillation sump product with water and a carboxylic acid having 1 to 4 C atoms. The phases generated are separated and cobalt is recovered from the carboxylic acid/water phase in the form of the corresponding carboxylic acid salt. Where appropriate, the corresponding carboxylic acid salt is transformed into another carboxylic-acid salt.

A second embodiment includes the steps of hydrogenating the cobalt containing residue obtained as the distillation sump product, separating the metallic cobalt which is obtained, reacting the metallic cobalt with an acid and where appropriate converting the cobalt salt so obtained into another cobalt salt.

12 Claims, No Drawings

METHODS FOR REPROCESSING COBALT CATALYSTS USED IN HYDROCARBOXYLATION

This is a division of application Ser. No. 516,435, filed July 25, 1983 now U.S. Pat. No. 4,521,526 which in turn is a continuation in part of application Ser. No. 203,393 filed Nov. 3, 1980, now abandoned.

CROSS-REFERENCES TO RELATED APPLICATIONS

Applicant claims priority under 35 U. S. C. 119 for applications Nos. P 29 49 939.6 and P 29 49 878.0, both filed Dec. 12, 1979 in the Patent Office of the Federal Republic of Germany.

The disclosure of applicant's copending U.S. patent application Ser. No. 125,482, filed Feb. 28, 1980 is incorporated herein to show the application of the cobalt catalysts of the present invention in hydrocarboxylation reactions.

BACKGROUND OF THE INVENTION

The field of the invention is catalysts used in the synthetic production of higher fatty acids and the present invention is particularly concerned with the recovery of cobalt catalysts used in the production.

The state of the art of the production of fatty acids or the corresponding fatty acid derivatives by reacting olefins with carbon monoxide and an appropriate compound containing a replaceable hydrogen atom such as water or alkanol in the presence of a catalyst containing a metal of Group VIII of the Periodic Table of elements and possibly also a promoter may be ascertained by reference to J. FALBE, "Synthesen mit Kohlenmonoxid", Springer published, Berlin, Heidelberg, New York, 1967 and U.S. Pat. Nos. 3,507,891 and 3,856,832, the disclosures of which are incorporated herein.

As a preferred embodiment of the reaction of olefins with carbon monoxide and a compound containing a replaceable hydrogen atom, where the reaction is called hydrocarboxylation, the reaction takes place in the presence of cobalt catalysts. An especially preferred embodiment consists in additionally using a promoter, in particular pyridine or a non-ortho-substituted alkylpyridine.

This homogeneously catalyzed reaction suffers from the substantial disadvantage that the relatively costly cobalt must be recovered from the reaction mixture in a form which permits its re-use as a catalyst.

The process disclosed in U.S. Pat. No. 3,856,832 solves this problem by carrying out the olefin reaction with carbon monoxide in the presence of an excess of alkanol and paraffin, or paraffin is added after the reaction is completed. In this manner a two-phase mixture is formed. The lower phase consists predominantly of alkanol and promoter and contains a maximum of about 97% of the cobalt used as catalyst. The upper paraffinic phase consists essentially of non-reacted olefin and reaction products.

The lower phase containing the catalyst still in active form, is used in the reaction. However, the advantage so obtained is more than negated by the loss of about 3% of the cobalt used. A hydrocarboxylation method can only be considered economically satisfactory when the cobalt in the paraffinic phase is also recovered. In view of the excess of alkanol and the addition of paraffin required for the method of U.S. Pat. No. 3,856,832, such reprocessing is very costly.

Another process for recovering the cobalt catalyst is described in U.S. Pat. No. 3,507,891. The method is characterized by recovering the cobalt together with the sump product from the reprocessing by distillation of the reaction mixture.

When the reaction mixture is subjected to an oxidizing treatment prior to reprocessing by distillation, for instance oxidizing with air, the catalyst is recovered in a form from which the active catalyst species is produced again only under the conditions of the hydrocarboxylation. It would appear that an oxidizing treatment of the reaction mixture can be dispensed with only when alkylpyridines are used as promoters. Thermostable complexes would be expected to form, and retain their activity, in the presence of these promoters under the conditions of distillation.

While the process of U.S. Pat. No. 3,507,891 does offer a way to widely recover the cobalt used, it nevertheless fails to provide, just as the method of U.S. patent application Ser. No. 125,482 fails to provide, a way for separating high boiling-point substances and other interfering contaminants which inevitably are formed as by-products in the hydrocarboxylation.

SUMMARY OF THE INVENTION

Having in mind the limitations of the prior art, it is an object of the present invention to develop as simple as possible a method which is extensively free of losses for the reprocessing of the cobalt catalyst used in hydrocarboxylation and which simultaneously permits the separation of undesired contaminations of high boiling-point compounds.

This object is achieved according to the present invention in a first embodiment where the reaction mixture following an oxidizing treatment is distilled and the cobalt sump product so produced is treated with water and a carboxylic acid having 1 to 4 C atoms, the phases so generated are separated and cobalt is recovered from the aqueous carboxylic-acid phase in the form of a carboxylic acid salt.

In a second embodiment, this object is achieved by hydrogenating the reaction mixture following the oxidizing treatment, by separating the metallic cobalt so obtained and by treating the separated metallic cobalt with an acid and then feeding it back into the process in the form of a compound soluble at least in one of the reagents.

DESCRIPTION OF THE PREFERRED EMBODIMENTS

In principle, the process of the present invention can be carried out in all hydrocarboxylation reactions which take place in the presence of a cobalt catalyst compound such as disclosed in U.S. Pat. No. 3,507,891 and U.S. patent application Ser. No. 125,482, filed on Feb. 28, 1980. Most of all, the selection of the olefin used is not critical, that is, both straight-chain or branched-chain alpha-olefins and olefins with internal double bonds are useful. However, olefins with more than one internal double bond, and olefins with more than one internal double bond comprising substituents, for instance aryl-, cyano-, carboximethyl- and hydroxyl-groups are also suitable.

As a rule, olefins having 2 to 40, preferably 4 to 20 C atoms are used, which are produced according to the state of the art. For instance, alpha-olefins are produced by Ziegler ethylene synthesizing reactions, or by wax cracking. Olefins with internal double bonds are made by dehydrogenation or chlorination and ensuing dehydrochlorination of paraffins.

In the last cited method, blends, that is mixtures of paraffins of different C numbers are used, whereby the olefins produced in turn lack uniform C numbers. Furthermore, all conceivable isomeric forms are present in these olefin mixtures.

Besides pure and possibly substituted olefins, olefins containing paraffin also are useful. There is a paraffin content because conversion is not complete in the olefin production, and the non-reacted paraffins are not separated, or are only partly separated.

Besides the olefin used, the compound containing a replaceable hydrogen which is reacted with the olefin and carbon monoxide also is not critical for the process of the present invention. Both water and alkanols having 1 to 20, preferably 1 to 4 C atoms, are useful.

It is furthermore not significant what kind of cobalt compound is used in the hydrocarboxylation. Cobalt carbonyls are just as suitable as carboxylic acid salts or salts of cobalt with inorganic acids. Preferably, those carboxylic acid cobalt salts are used which have anions formed as the corresponding carboxylic acids or carboxylic acid esters in the hydrocarboxylation.

When in addition to the cobalt compound a promoter is used, preferably the promoter is pyridine, all non-ortho-substituted alkylpyridines or N-methylpyrrolidone.

Finally, the reaction conditions in which the hydrocarboxylation is carried out are not critical for the process of the present invention. As a rule, the hydrocarboxylation methods are implemented at temperatures from about 80° to 300°, preferably 150° to 220° C., and at carbon monoxide pressures from about 10 to 800, preferably 100 to 300 bars.

What is critical for the process of the present invention, however, is the oxidizing treatment of the reaction mixture before the recovery of the cobalt. This oxidizing treatment is carried out by means of oxygen or an oxygenated gas, preferably air, at temperatures from about 20° to 150°, preferably 70° to 120° C. Such a treatment is disclosed in U.S. Pat. No. 3,507,891, column 4, lines 21–43 and in U.S. patent application Ser. No. 125,482, filed Feb. 28, 1980, page 7, first full paragraph, which is not yet part of the state of the art, and it is carried out until the cobalt compounds, which in the subsequent reprocessing by distillation result in metallic cobalt, are destroyed by oxidation.

In the following reprocessing by distillation, the volatile parts of the reaction mixture are separated either in one step or stepwise at sump temperatures up to 350° C. The cobalt content of the distillation sump product so obtained amounts to about 2 to 30, preferably 4 to 15% by weight.

The cobalt residue can be reprocessed either as a whole or in part in the process of the present invention. When partial reprocessing is chosen, the proportion of the cobalt residue to be reprocessed depends on the catalytic activity desired for the hydrocarboxylation, the admissible amount in ballast materials such as high boiling-point substances, and the cost expenditure required for the reprocessing.

It may be appropriate to dilute the cobalt residue with one or more solvents so as to handle the residue more conveniently. Suitable solvents are those which in the ensuing treatment with water and carboxylic acid do not hamper the formation of two separate phases. Suitable solvents are therefore paraffins, preferably those having 5 to 10 C atoms, or aromatic substances such as benzene, toluol or xylene.

Carboxylic acids having 1 to 4 C atoms are suitable to treat the cobalt residue, which may be diluted with solvents. Preferably acetic acid and/or propionic acid are used. At least 2 moles of carboxylic acid per gram-atom of cobalt are required. As a rule from about 2 to 250, preferably 2 to 100 moles of carboxylic acid are used per gram-atom of cobalt.

It is not critical for the process of the present invention whether the water required for treatment and separation is added together with the carboxylic acid or only after the addition of carboxylic acid.

The water is added in an amount sufficient to cause a separation into an upper organic phase and a lower aqueous carboxylic acid phase containing the cobalt in dissolved form. In general, the water is present in a proportion from about 0.1 to 10 times the amount by weight of the carboxylic acid.

The treatment of the cobalt catalyst compound residue is carried out in any suitable apparatus, for instance agitating vessels, cascaded agitated vessels and counterflow extractors.

As a rule the treatment temperature should not exceed the boiling point of the component having the lowest boiling-point in the 2-phase mixture. Preferably the treatment temperature is in the range between about 20° and 100° C.

Following the treatment with carboxylic acid and water, and possibly after some waiting time, the separation of the phases formed takes place in appropriate apparatus, for instance a separating funnel or a settling container. This separate isolation stage can be eliminated if an adequate phase separation takes place during the treatment, for instance in the counterflow extractor.

Both the treatment of the cobalt catalyst compound residue with carboxylic acid and water and any required ensuing phase separation can be repeated in continuous or discontinuous manner for the purpose of enhancing the cobalt recovery.

Any combined cobalt phases are subsequently reprocessed by separating water and excess carboxylic acid, for instance by distillation. The carboxylic acid cobalt salt remains.

When and to the extent this carboxylic acid cobalt salt does not dissolve in one of the reagents used for the hydrocarboxylation and cannot be easily fed back in the form of the solution into the hydrocarboxylation process, a last stage is required for its conversion. This conversion consists in being reacted with a carboxylic acid such that the cobalt salt of the carboxylic acid is soluble in at least one of the reagents. For instance cobalt acetate, which does not dissolve in higher alkanols, olefins and any promoters used, can be converted for instance, by means of 2-ethylhexanoic acid into the so-called cobalt octoate, the octoate being soluble in alkanols having a C number equal to or larger than 2. The acetic acid released in the above disclosed conversion can be separated by distillation and can be fed back into the reprocessing cycle.

The organic phase more or less freed of cobalt is either discarded or, if required by process economies, reprocessed. This can take place, for instance, by distillation. Any solvent added to dilute the cobalt residue compound can be recovered in this procedure and the carboxylic acids produced in this stage can be re-used at a suitable place in the process of the present invention.

According to the second principal embodiment of the present invention, the distillation sump product to be reprocessed is subjected at increased pressure and elevated temperature to a hydrogenating treatment which is surprisingly carried out without using any additional hydrogenating catalyst. As a rule, the temperatures used are between about 20° and 300° C., preferably between 140° and 220° C. The hydrogen pressure required for hydrogenation as a rule is about 50 to 500 bars, preferably 150 to 300 bars.

Even though the hydrogenation of the cobalt containing sump product can be implemented also in the absence of a solvent, solvents nevertheless are suitably used. Such solvents include alkanols, for instance preferably methanol, paraffins, preferably those having 5 to 8 C atoms such as the $C_5$ blend, hexane or cyclohexane, or carboxylic acids, preferably acetic acid or propionic acid. The amount by weight of the solvent is from 0.1-fold to 10-fold that of the distillation sump product.

Following a hydrogenation time up to 10 hours, preferably up to 5 hours, the reaction mixture obtained is isolated for instance by filtration into a residue consisting of metallic cobalt and an organic phase. Appropriately the operation takes place in an atmosphere of an inert gas such as nitrogen or argon, so that the cobalt is obtained in a very finely distributed form and therefore a pyrophoric form.

The organic phase obtained in this isolation is suitably reprocessed by distillation. Thereby any solvent used in the hydrogenation is recoverable and the remaining products where appropriate also are made use of.

Because in general the metallic cobalt as such cannot be fed back into a hydrocarboxylation process, it is converted into a salt by treatment with an inorganic acid or with a carboxylic acid. A reaction of the metallic cobalt with $C_1$- to $C_4$-carboxylic acids, preferably acetic acid and/or propionic acid, is found to be especially advantageous. To shorten the dissolution process of the metallic cobalt in the organic acids, appropriately the operation is carried out at higher temperature, for instance with reflux in the presence of water, while simultaneously an oxygenated gas, for instance air, is passed through.

When the cobalt salt so obtained is insoluble or inadequately soluble in the reagents used for the hydrocarboxylation, then a transformation is required as the last step. This transformation comprises a reaction with a given carboxylic acid so that its cobalt salt is soluble at least in one of the reagents used. For instance, cobalt acetate, which is insoluble in the higher alkanols, olefins and any promoters added, is converted by means of 2-ethylhexanoic acid for instance, into the so-called cobalt octoate which is soluble in alkanols with a C number equal to or larger than 2. The acetic acid released in the above reaction is isolated by distillation and fed back into the reprocessing procedure.

As already disclosed, the process of the present invention can be used successfully in all hydrocarboxylation procedures employing a cobalt catalyst compound.

Unless indicated otherwise, all percentage data are by weight, including the examples which illustrate the process of the present invention.

EXAMPLE 1

Hydrocarboxylation 1,680 g of a statistical isomer mixture of linear dodecenes with internal double bonds (the proportion of 1-dodecene is less than 1%), 800 g of methanol, 167 g of a 10% cobalt-tridecanoate and 279 g of gamma-picoline are reacted in a 5 liter agitated stainless steel autoclave at 180° C. with CO with an $H_2$ content of 2% by volume at 200 bars hot pressure. After 3 hours, the reaction is stopped, the olefin conversion being 87%.

Oxidizing Treatment of the Reaction Output

The total reaction output of 3,126 g is treated in a trickling column (1 m long, inside diameter 2.5 cm) filled with Raschig rings at 80° C. in counterflow with 100 liters per hour of air. The dwell time of the liquid phase fed in at the top in the trickling column is 15 min.

Catalyst Reprocessing

Methanol, gamma-picoline, unreacted dodecene and tridecanoic acid methylester are separated from the above pretreated reaction output by stepwise distillation. After the separation of the ester fraction, a 198 g residue having a cobalt content of 8.43% remains.

The cobalt residue is heated under reflux together with a mixture of 400 g of acetic acid and 400 g of water for 1 hour. The phases so produced are separated in a heated separating funnel at 90° C. The weight of the upper organic phase is 188 g. The weight of the lower aqueous acetic-acidic phase is 810 g, its cobalt content being 2.04%. Thus, 99.1% of the overall cobalt used as hydrocarboxylation catalyst are in the aqueous acetic-acidic phase.

The upper organic phase is again reacted with 376 g of a mixture of equal parts by weight of acetic acid and water, boiled under reflux for 15 min, and the phases so obtained are separated in a heated separating funnel at 90° C. The upper organic phase so obtained has a weight of 184 g. The weight of the lower aqueous acetic-acid phase is 380 g and its cobalt content is 0.037%.

The two aqueous acetic-acidic phases obtained by extraction and together containing 99.95% of the cobalt used as hydrocarboxylation catalyst are combined and then concentrated in a rotary evaporator under water-jet vacuum and at a bath temperature of 55° C. until dry. 63.4 g of a violet crystalline solid with a cobalt content of 26.3% are obtained.

Re-Use of the Recovered Cobalt as Hydrocarboxylation Catalyst

The hydrocarboxylation described at the beginning of Example 1 is repeated under the same conditions except that the catalyst now being used is a methanol-dissolved mixture of 63.4 g of the violet crystalline solid and 33 mg of cobalt acetate (to replenish the cobalt losses). The reaction again is stopped after 3 hr and its results are the same as from the hydrocarboxylation initially described.

EXAMPLE 2

The hydrocarboxylation described in Example 1 is repeated, except that 111.3 grams of cobalt naphthenate with a cobalt content of 15% are used as the hydrocarboxylation catalyst.

The oxidizing treatment of the hydrocarboxylation output is the same as in Example 1.

132.7 g of residue with a cobalt content of 12.6% remain as the sump product from a stepwise reprocessing by distillation of the oxidation-pretreated reaction mixture.

This residue is reprocessed in the same manner as in Example 1 by a two-fold extraction. The combined aqueous/acetic-acidic phases are concentrated until dry as in Example 1 and produce 64.5 g of a violet, crystalline solid with a cobalt content of 25.8%. This amounts to a cobalt recovery of 99.7%.

EXAMPLE 3

Example 1 is repeated except that only 30% of the cobalt residue remaining after the reprocessing by distillation of the oxidation-treated hydrocarboxylation output are reprocessed. The amounts of acetic acid and water used for the extraction treatment are correspondingly decreased in regard to the lesser amount of residue. The end product of the catalyst reprocessing are 19.2 g of a violet, crystalline solid containing 26.1% cobalt. This corresponds to a cobalt recovery of 99.9% referred to the reprocessed portion of the cobalt residue.

19.2 g of violet crystalline solid and 20 mg of cobalt acetate (to replenish cobalt losses) are dissolved in methanol and are used together with the 70% non-reprocessed cobalt residue as the hydrocarboxylation catalyst. The same hydrocarboxylation conditions stated in the beginning of Example 1 are used. After a reaction of 3 hours, the olefin conversion is 86%.

EXAMPLE 4

Example 1 is repeated, except that the cobalt residue remaining as the sump product from the reprocessing by distillation is reacted with 200 ml of n-hexane before reprocessing.

The degree of cobalt recovery thereby is 99.97%.

EXAMPLE 5

Example 1 is repeated, except that in lieu of the acetic acid used for extractive reprocessing, the same amount by weight of propionic acid is used.

The end product of the catalytic reprocessing is a violet, pasty product soluble in alkanols such as methanol and ethanol and also in gamma-picoline which contains 99.85% of the cobalt used as hydrocarboxylation catalyst.

EXAMPLE 6

Example 1 is repeated except that only 50% of the amount of water stated in Example 1 is used for the extractive catalytic reprocessing.

The degree of the cobalt recovery is 99.85%.

EXAMPLE 7

Example 1 is repeated, except that in lieu of the 800 g of methanol used in the hydrocarboxylation, the same amount by weight of ethanol is used.

In order to feed back in the form of a solution the violet crystalline solid containing 99.9% of the cobalt used in the catalyst reprocessing and remaining as its end product, in a reagent used in the hydrocarboxylation, into the reaction, this solid is converted into another carboxylic acid salt: 64.2 g of the violet crystalline solid inadequately soluble in any of the reagents are reacted with 150.3 g of 2-ethylhexanoic acid and heated in a water-jet vacuum until no more acetic acid and no more water are distilled off.

The cobalt octoate so obtained following replenishment of the cobalt losses is used again in the form of an ethanol solution as a catalyst for the hydrocarboxylation. The same conditions as at the beginning of Example 7 are observed. There is no difference in the reaction outcomes in the two hydrocarboxylation batches of Example 7.

EXAMPLE 8

Example 1 is repeated, except that 1,960 g of alpha-tetradecene are used in lieu of dodecene.

The degree of the cobalt recovery is 99.88%.

EXAMPLE 9

Hydrocarboxylation 2,016 g of a mixture of 40% by mole of n-undecene, 20% by mole of n-tridecene and 40% by mole of n-dodecene (the olefins are present always as a statistical isomer mixture with an alpha-olefin proportion of less than 1%), 800 g of methanol, 167 g of a mixture of dodecanoic acidic cobalt, tridecanoic acidic cobalt and tetradecanoic acidic cobalt (cobalt content is 10%) and 279 g of gamma-picoline are reacted with CO with an $H_2$ content of 2% by volume at 180° C. at 200 bars hot pressure in a 5 liter agitated stainless steel autoclave. After 3 hours the reaction is stopped at an olefin conversion of 83%.

Oxidizing Treatment of the Reaction Product

The entire reaction product of 3,495 g is treated in a trickling column 1 m long, 2.5 cm inside diameter and filled with Raschig rings at 80° C. in counterflow with 100 liters per hour of air. The dwell time of the upwardly incoming phase in the trickling column is 15 minutes.

Catalyst Reprocessing

From the reaction substance so pretreated, methanol, gamma-picoline, unreacted olefin and the mixture of dodecanoic, tridecanoic and tetradecanoic acid methyl-esters are separated by stepwise distillation. After the ester fraction is removed, a residue of 205 g with a cobalt content of 8.15% remained.

The cobalt residue is placed in 410 g of n-hexane and hydrogenated in a 2 liter agitated stainless steel autoclave for 5 hours at 180° C. and a $H_2$ hot pressure of 300 bars. The autoclave product is filtered in an $N_2$ protective atmosphere, the filter cake is rinsed three times with a total of 100 ml of n-hexane. The gray-black pulvurulent filter cake weighs 19.72 g and its cobalt content is 83.5%. Thus, 98.6% of the cobalt used as the hydrocarboxylation catalyst is in the filter cake.

The hexane is recovered by distillation from the filtrate. The cobalt filter cake is boiled in a mixture of 100 g of acetic acid and 100 g water for 2 hours with reflux. 30 liters per hour of air are passed through the boiling mixture. The violet solution so obtained is concentrated in a rotary evaporator under water-jet vacuum and at a bath temperature of 55° C. until dry. 64.1 g of a violet crystalline solid with a cobalt content of 25.7% are obtained.

Re-Use of the Recovered Cobalt as Hydrocarboxylation Catalyst

The hydrocarboxylation described at the beginning of Example 9 is repeated under the same conditions except that now the catalyst used is a mixture of 64.1 g of the violet crystalline solid and 920 mg of cobalt acetate (to replenish cobalt losses), dissolved in methanol. The reaction again is stopped after 3 hours and offers the same results as the hydrocarboxylation described initially.

EXAMPLE 10

The hydrocarboxylation of Example 9 is repeated except that 111.3 g of cobalt naphthenate with a cobalt content of 15% are used as the hydrocarboxylation catalyst.

The oxidizing treatment of the reaction substance from the hydrocarboxylation takes place under the same conditions as in Example 9.

The sump product from a stepwise reprocessing by distillation of the oxidation-pretreated mixture of reaction consists of 137.5 g of a residue with a cobalt content of 12.13%.

This residue is hydrogenated under the same conditions as in Example 9. The cobalt filter cake obtained from filtration is dissolved as in Example 9. The solution obtained following concentration until dry is 65.1 g of a violet crystalline solid with a cobalt content of 25.4%. This corresponds to a cobalt recovery of 99.0%.

EXAMPLE 11

Example 9 is repeated except that only 20% of the cobalt residue remaining after the reprocessing by distillation of the oxidized hydrocarboxylated substance are reprocessed. The amount of n-hexane used as the solvent for the hydrogenation is correspondingly decreased. The end product of the catalyst reprocessing is 12.9 g of violet crystalline solid containing 25.6% cobalt. This corresponds to a cobalt recovery of 98.8% referred to the reprocessed portion of the cobalt residue.

The violet crystalline solid and 160 mg of cobalt acetate (to replenish the cobalt losses) are dissolved in methanol and are used together with the 80% of the non-reprocessed catalyst residues as the hydrocarboxylation catalyst. The conditions of the hydrocarboxylation initially described in Example 9 are observed. After a reaction of 3 hours, the olefin conversion is 83%.

EXAMPLE 12

Example 9 is repeated except that the hydrogenating catalyst reprocessing is carried out at 160° C. and 200 bars $H_2$ hot pressure.

The degree of the cobalt recovery so achieved is 98.5%.

EXAMPLE 13

Example 9 is repeated, except that the same amount by weight of methanol is used in lieu of n-hexane as the solvent for the hydrogenating catalyst reprocessing.

The cobalt recovery so achieved is 99.0%.

EXAMPLE 14

Example 13 is repeated except that only half the amount by weight of methanol is used as the solvent for the hydrogenating catalyst reprocessing.

The cobalt recovery so achieved is 98.7%.

EXAMPLE 15

Example 9 is repeated but in lieu of 800 g of methanol, the same amount by weight of ethanol is used in the hydrocarboxylation.

So that the violet crystalline solid containing 98.4% of the cobalt used as hydrocarboxylation catalyst and remaining as the end product of the catalyst reprocessing can be employed again dissolved in one of the reagents for the hydrocarboxylation which is fed back into the reaction, it is converted into another carboxylic acid salt:

66.2 g of the violet crystalline solid, which is inadequately soluble in all of the reagents, are reacted with 147.3 g of a mixture of dodecanoic, tridecanoic and tetradecanoic acids obtained by the hydrocarboxylation of Example 9 and heated long enough in a water-jet vacuum until no more acetic acid and water distill off. The fatty acid cobalt so obtained after replenishment of the cobalt losses is used again in the form of an ethanol solution as the catalyst for the hydrocarboxylation. The same conditions as at the beginning of Example 15 are observed. The differences in the reactions obtained from the two batches used in the hydrocarboxylation of Example 15 are nil.

EXAMPLE 16

Example 15 is repeated except that the cobalt filter cake obtained by filtration is reprocessed using propionic acid instead of acetic acid, and in the same amount by weight.

The end product of the catalyst reprocessing is a pasty violet product soluble in ethanol and containing 98.5% of the cobalt used as hydrocarboxylation catalyst.

EXAMPLE 17

Example 9 is repeated except that 1,400 g of alpha-decene are used in lieu of the mixture of olefins with internal double bonds.

The cobalt recovery so achieved is 98.9%.

EXAMPLE 18

Example 1 is repeated, except that pyridine is used in place of gamma-picoline in the hydrocarboxylation. The degree of cobalt recovery is the same as in Example 1.

EXAMPLE 19

Example 9 is repeated, except that pyridine is used in place of gamma-picoline in the hydrocarboxylation. The degree of cobalt recovery is the same as in Example 9.

I claim:

1. A method for reprocessing cobalt catalyst from cobalt salts of carboxylic acids having 1 to 4 carbon atoms used in the reaction of olefins having 2 to 40 carbon atoms with carbon monoxide and an alkanol having 1 to 20 carbon atoms, comprising:
    (a) reacting said olefins with said carbon monoxide and said alkanol in the presence of said cobalt catalyst to form a reaction output;
    (b) oxidizing said reaction output with countercurrent oxygenated gas at a temperature from about 20° to 150° C. to form a pretreated reaction output;
    (c) carrying out a stepwise distillation of said pretreated reaction output, separating an ester fraction and leaving a distillation sump product containing a cobalt residue having a cobalt content of about 2 to 30% by weight;
    (d) treating said cobalt residue with water and a given carboxylic acid having 1 to 4 carbon atoms in a proportion from about 0.1 to 10 times the amount by weight of said given carboxylic acid at a temperature of about 20°–100° C. to form a first upper organic phase and a first lower aqueous acidic phase;

(e) separating said first upper organic phase from said first lower aqueous acidic phase;

(f) treating said separated first upper organic phase with said water and given carboxylic acid in a proportion from about 0.1 to 10 times the amount by weight of said given carboxylic acid at a temperature of about 20° to 100° C. to form a second upper organic phase and a second lower aqueous acidic phase;

(g) separating said second upper organic phase from said second lower aqueous acidic phase;

(h) recovering cobalt in the form of the carboxylic acid salt corresponding to said given carboxylic acid from said first and second separated lower aqueous acidic phases; and (i) recirculating said carboxylic acid salt as said cobalt catalyst with a recovery of 98.4 to 99.97% of said cobalt catalyst.

2. The method of claim 1, wherein said temperature of step (b) is 70°–120° C.

3. The method of claim 2, further comprising transforming said corresponding carboxylic acid salt into a second carboxylic salt.

4. The method of claim 2, wherein gamma-picoline is added as a promoter to said catalyst and said temperature of step (b) is 80° C. and step (b) is carried out for a period of 15 minutes and said water and carboxylic acid of steps (d) and (f) are equal proportions of acetic acid and water, said residue is 8.43% cobalt and the ratio of said residue to acetic acid is ½.

5. The method of claim 2, wherein gamma-picoline is added as a promoter to said catalyst and said temperature of step (b) is 80° and step (b) is carried out for a period of 15 minutes and said water and carboxylic acid of steps (d) and (f) are equal proportions of propionic acid and water, said residue is 8.43% cobalt and the ratio of said residue to propionic acid is ½.

6. The method of claim 2, wherein gamma-picoline is added as a promoter to said catalyst and said temperature of step (b) is 80° C. and step (b) is carried out for a period of 15 minutes and said water and carboxylic acid of steps (d) and (f) are two parts acetic acid to one part water, said residue is 8.43% cobalt and the ratio of said residue to acetic acid is ½.

7. The method of claim 2, wherein said given carboxylic acid is acetic acid or propionic acid.

8. The method of claim 3, wherein said second carboxylic acid salt is recycled to step (a) as said cobalt catalyst.

9. The method of claim 2, wherein pyridine is added as a promoter to said catalyst and said temperature of step (b) is 80° C. and step (b) is carried out for a period of 15 minutes and said water and carboxylic acid of steps (d) and (f) are equal proportions of acetic acid and water, said residue is 8.43% cobalt and the ratio of said residue to acetic acid is ½.

10. The method of claim 2, wherein said temperature of step (b) is 80° C. and step (b) is carried out for a period of 15 minutes, and said water and carboxylic acid of steps (d) and (f) are equal proportions of acetic acid and water.

11. The method of claim 2, wherein said temperature of step (b) is 80° C. and Step (b) is carried out for a period of 15 minutes and said water and carboxylic acid of steps (d) and (f) are equal proportions of propionic acid and water.

12. The method of claim 2, wherein said temperature of step (b) is 80° C. and step (b) is carried out for a period of 15 minutes and said water and carboxylic acid of steps (d) and (f) are two parts acetic acid to one part of water.

* * * * *